(12) United States Patent
Matsuo et al.

(10) Patent No.: US 8,003,047 B2
(45) Date of Patent: Aug. 23, 2011

(54) VEHICLE EFFICACIOUS CONSTITUENTS SUPPLY APPARATUS

(75) Inventors: Noriyoshi Matsuo, Tokyo (JP); Takashi Kondo, Tokyo (JP)

(73) Assignee: Fuji Jukogyo Kabushiki Kaisha, Shinjuku-ku, Tokyo (JP)

( * ) Notice: Subject to any disclaimer, the term of this patent is extended or adjusted under 35 U.S.C. 154(b) by 521 days.

(21) Appl. No.: 12/011,000

(22) Filed: Jan. 31, 2008

(65) Prior Publication Data

US 2008/0207107 A1  Aug. 28, 2008

(30) Foreign Application Priority Data

Feb. 1, 2007  (JP) ................. P.2007-022990

(51) Int. Cl.
*A61L 9/00* (2006.01)
*G05D 9/00* (2006.01)
*A62B 7/08* (2006.01)
*B60K 31/00* (2006.01)
*B60K 28/00* (2006.01)
*B60K 28/12* (2006.01)
*F02M 47/02* (2006.01)
*B05B 1/08* (2006.01)

(52) U.S. Cl. .............. 422/5; 422/1; 422/2; 422/107; 422/108; 422/117; 422/119; 422/123; 180/272; 180/282; 180/170; 239/87; 239/88; 239/102.2

(58) Field of Classification Search ........... 442/1–2, 442/5, 107–108, 117, 119, 123; 180/272, 180/282, 170; 239/87, 88, 102.2
See application file for complete search history.

(56) References Cited

U.S. PATENT DOCUMENTS

2005/0126841 A1 * 6/2005 Isaji et al. .................. 180/272

FOREIGN PATENT DOCUMENTS

| JP | 2006-280748 | 10/2006 |
|----|-------------|---------|
| JP | 2006-282083 | 10/2006 |
| JP | 2006-282084 | 10/2006 |
| JP | 2006-282085 | * 10/2006 |

OTHER PUBLICATIONS

Machine English Translation of the Detailed Description section and the Drawings section of JP 2006-282085.*

* cited by examiner

*Primary Examiner* — Jill Warden
*Assistant Examiner* — Monzer R Chorbaji
(74) *Attorney, Agent, or Firm* — McGinn IP Law Group, PLLC

(57) ABSTRACT

A vehicle efficacious constituents supply apparatus 10 includes a main unit 13 including an air gun and a subunit 15 including an air gun. A curling ring V1 of air containing aromatic constituents is projected from the main unit 13 towards an efficacious area A, while a curling ring V2 of air is projected from the subunit 15 towards the efficacious area A. A control unit for controlling projection timings of curling rings V1, V2 includes an alarming mode in which a projection interval at which curling rings v1 are projected is set shorter than a projection interval at which curling rings V2 are projected, and by executing this alarming mode, curling rings V2 can be applied to an occupant without causing the curling rings V2 so projected to disappear in the efficacious area A.

13 Claims, 8 Drawing Sheets

EFFICACIOUS MODE

ALARMING MODE

ALARMING MODE

VEHICLE EFFICACIOUS CONSTITUENTS SUPPLY APPARATUS

BACKGROUND OF THE INVENTION

The disclosure of Japanese Patent Application No. 2007-022990 filed on Feb. 1, 2007 including the specification, drawings and abstract is incorporated herein by reference in its entirety.

The present invention relates to a vehicle efficacious constituents supply apparatus for supplying efficacious constituents to an occupant of a vehicle.

There have been proposed supply apparatuses for supply aromatic constituents or moisture constituents from vents of an air conditioning system in order to maintain a good environment within a passenger compartment. Once aromatic constituents are supplied from the vents, however, the aromatic constituents so supplied eventually fill the passenger compartment, and hence, not only is a large amount of aromatic constituents necessary but also it has become difficult to provide environments according to tastes of occupants within the passenger compartment.

To cope with this, there have been proposed supply apparatuses in which curling rings of aromatic constituents or moisture contents are projected towards an occupant (refer to, for example, Patent Document Nos. 1 to 4). Since the apparatuses allow aromatic constituents or the like to be supplied locally, it becomes possible to provide environments which satisfy the tastes of the occupants within the passenger compartment by employing a small amount of aromatic constituents.

[Patent Document No. 1] JP-A-2006-280748
[Patent Document No. 2] JP-A-2006-282083
[Patent Document No. 3] JP-A-2006-282084
[Patent Document No. 4] JP-A-2006-282085

Incidentally, in the supply apparatus described in Patent Document No. 3, an organism sensor for detecting an organic signal such as the heart rate of an occupant is provided, and when the organism sensor detects that the occupant gets sleepy, aromatic constituents having an awakening effect are made to be supplied towards the occupant. Although the sleepiness arising in the occupant is eliminated to enhance the safety in driving by supplying the aromatic constituents having the awakening effect in this way, since there exists an occasion where in the event that the degree of awakening of the occupant is decreased remarkably, the degree of awakening of the occupant necessary for safety driving cannot be recovered only by the aromatic constituents, a further improvement is in demand which can promote the safety operation of the vehicle in driving.

SUMMARY OF THE INVENTION

An object of the invention is to provide a vehicle efficacious constituents supply apparatus which can promote the safety operation of the vehicle by the occupant in driving while maintaining a good environment within the passenger compartment.

With a view to attaining the object, according to a first aspect of the invention, there is provided a vehicle efficacious constituents supply apparatus including:

a first projecting section for projecting a first curl of air towards a first predetermined position, a second projecting section for projecting a second curl of air towards a second predetermined position, a constituents supply section for supplying efficacious constituents to at least either of the first curl of air and the second curl of air, and a projection control section for controlling projection timings of the first curl of air and the second curl of air, wherein the projection control section includes, as projection modes, an efficacious mode in which efficacious constituents are diffused by causing the first curl of air and the second curl of air to collide with each other and an alarming mode for causing at least either of the first curl of air and the second curl of air to collide against an occupant without causing the curls of air to collide with each other.

According to a second aspect of the present invention, there is provided the vehicle efficacious constituents supply apparatus as set forth in the first aspect, further including:

an awakening detection section for detecting a degree of awakening of the occupant, wherein the projection control section executes the alarming mode based on the degree of awakening of the occupant.

According to the invention, since in addition to the efficacious mode in which the first curl of air and the second curl of air are made to collide against each other so as to diffuse efficacious constituents, the alarming mode is provided to the projection control section which controls the projection timings of the first curl of air and the second curl of air in which at least either of the first curl of air and the second curl of air is made to collide with the occupant without causing the curls of air to collide against each other, the degree of awakening of the driver can be enhanced by employing the alarming mode, thereby making it possible to promote the safety operation of the vehicle by the occupant in driving.

DETAILED DESCRIPTION OF THE PREFERRED EMBODIMENTS

Figure 1:
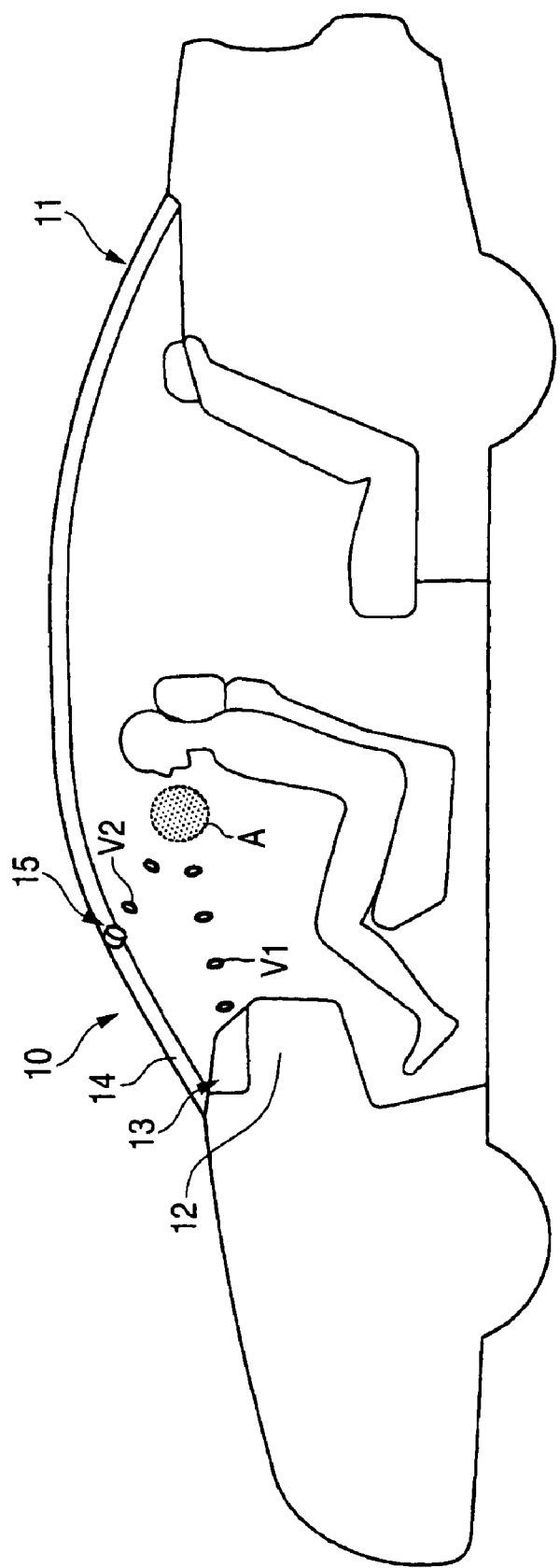
FIG. 1 is an explanatory drawing showing a vehicle which is equipped with a vehicle efficacious constituent supply apparatus which is one embodiment of the invention.

Hereinafter, an embodiment of the invention will be described in detail based on the accompanying drawings. FIG. 1 is an explanatory drawing showing a vehicle 11 which is equipped with a vehicle efficacious constituents supply apparatus 10 (hereinafter, referred to as a supply apparatus) which is an embodiment of the invention. In addition, FIG. 2 is a block diagram showing the configuration of the supply apparatus 10, and FIG. 3 is an explanatory drawing showing an interior configuration of an air gun 16 fitted on the supply apparatus 10.

As is shown in FIG. 1, the supply apparatus 10 for supplying efficacious constituents (such as aromatic constituents) towards an occupant includes a main unit 13 which is installed in an instrument panel portion 12 of a vehicle body and a subunit 15 which is installed in a front pillar portion of the vehicle body. Curling rings of air (first curls of air) V1 containing efficacious constituents are projected towards a predetermined efficacious area A from the main unit 13, while curling rings of air (second curls of air) V2 are projected towards the predetermined efficacious area A from the subunit 15. The curling rings V1, V2 are projected in such a manner as to collide against each other in the efficacious area A which is set in front of the nose of the occupant, thereby making it possible to diffuse the efficacious constituents contained in the curling rings V1 in the efficacious area A. In this way, it becomes possible to supply only efficacious constituents to the occupant without causing him or her to feel a sensation of physical disorder due to air pressure by causing the pair of curling rings V1, V2 to collide against each other to disappear.

Figure 2:
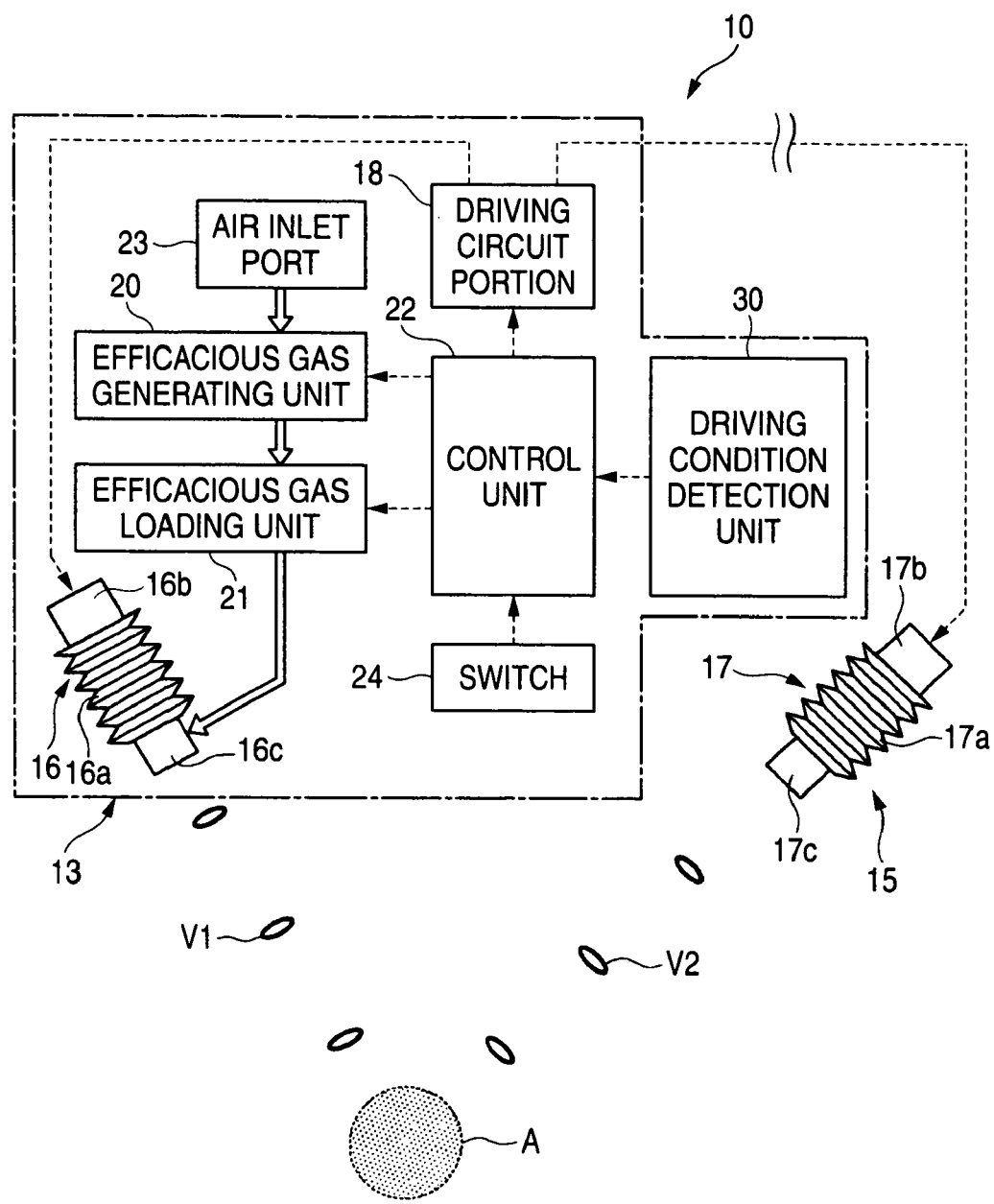
FIG. 2 is a block diagram showing the configuration of the vehicle efficacious constituents supply apparatus.
Figure 3A:
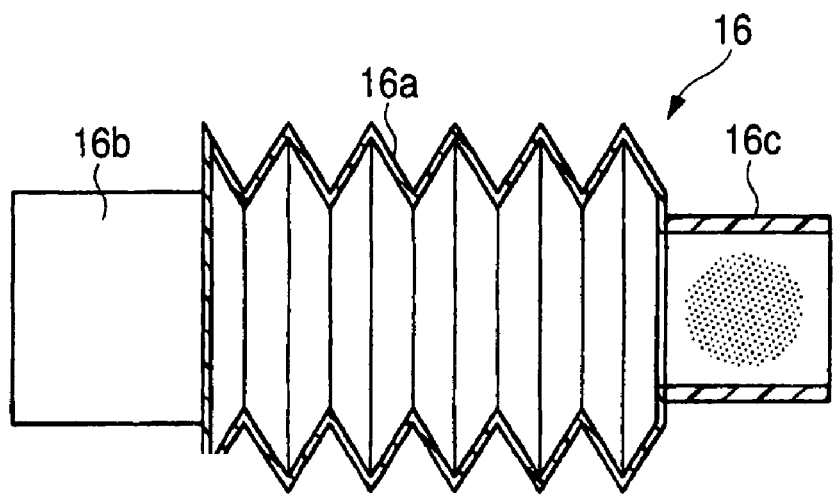
FIG. 3 is an explanatory drawing showing an interior configuration of an air gun provided in the vehicle efficacious constituents supply apparatus.
Figure 3B:
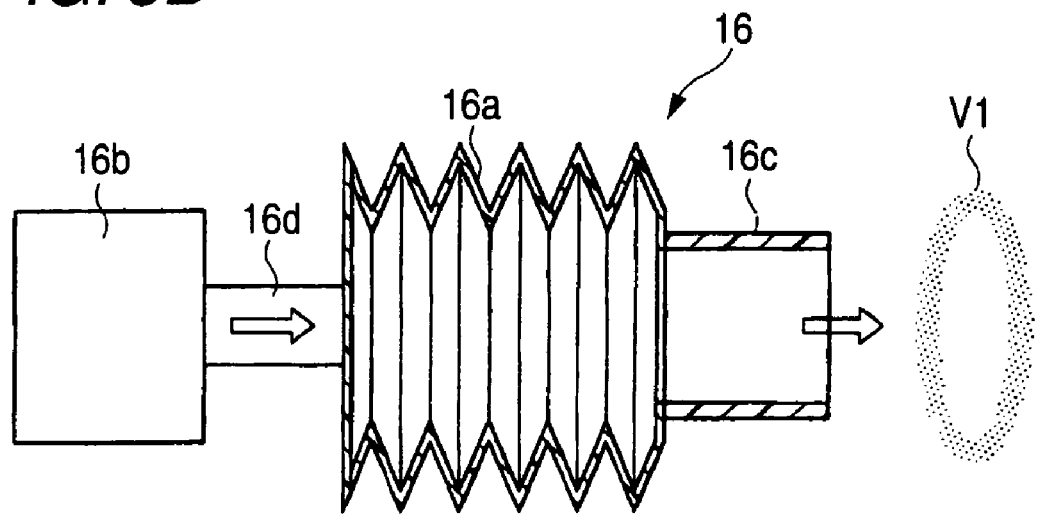

As is shown in FIG. 2, an air gun 16 is provided in the main unit 13 as a first projection section, and curling rings V1 which contain efficacious constituents are projected from this air gun 16. As is shown in FIG. 3, the air gun 16 is made up of a corrugated pump main body 16a which is made to freely extend and contract, a pump driving unit 16b for extending and contracting the pump main body 16a, and a cylindrical gun barrel portion 16c which is filled with efficacious constituents. In addition, a rod member 16d is built in the pump driving unit 16b in such a manner as to be driven back and forth, and this rod member 16d is driven by an electric motor, not shown, which resides in the pump driving unit 16b. In addition, after efficacious constituents are filled in the gun barrel 16c as is shown in FIG. 3A, the rod member 16d is caused to move forwards so as to quickly contract the pump main body 16a as is shown in FIG. 3B, whereby air within the pump main body 16a can be projected together with efficacious constituents in the gun barrel 16c as a curling ring V1.

In addition, as is shown in FIG. 2, an air gun 17 is provided in the subunit 15 as a second projection section for projecting curling rings V2 in such a manner as to collide against curling rings V1. The air gun 17, which includes a pump main body 17a, a pump driving unit 17b and a gun barrel portion 17c, has the same construction as that of the air gun 16, but efficacious constituents are filled in no case in the gun barrel portion 17c of the air gun 17, whereby curling rings V2 which is made up of only air are made to be projected from the air gun 17. In addition, as with the air gun 16 that has been described before, efficacious constituents may be filled in the gun barrel portion 17c of the air gun 17, so that curling rings V2 which contain efficacious constituents are projected from the air gun 17.

A driving circuit portion 18, which is connected to both the pump driving units 16b, 17b, is provided in the main unit 13 for curling rings V1, V2 to be projected by driving the air guns 16, 17. A projection signal (a projection timing) which is operated by a control unit (a projection control section) 22, which will be described later, is inputted into the driving circuit portion 18, which then controls a diving current for the pump driving units 16b, 17b based on the projection signal. Then, when the driving current is supplied to the pump driving portions 16b, 17b, curling rings V1, V2 are projected from the respective air guns 16, 17 at predetermined projection timings.

In addition, an efficacious gas generating unit 20 for generating aromatic constituents as efficacious constituents is provided in the main unit 13 so as to supply efficacious constituents to the air gun 16 of the main unit 13, and an efficacious gas loading unit 21 is provided for sending aromatic constituents into the gun barrel portion 16c of the air gun 16. Namely, the efficacious gas generating unit 20 and the efficacious gas loading unit 21 are made to function as a constituent supply section. The efficacious gas generating unit 20 is made up of a plurality of aroma containers, not shown, in which aromatic constituents are reserved and solenoid valves, not shown, for controlling the open and closed states of the aroma containers, while the efficacious gas loading unit 21 is made up of a pressure delivery pump, not shown, for delivering under pressure aromatic constituents towards the gun barrel portion 16c. Then, by executing a switching control of the solenoid valves and a driving control of the pressure delivery pump in response to a control signal from the control unit 22, which will be described later, efficacious constituents are made to be supplied to the gun barrel portion 16c of the air gun 16 together with air taken in from an air inlet port 23.

The control unit 22 which outputs control signal to the driving circuit portion 18, the solenoid valves, and the pressure delivery pump includes a microprocessor (CPU), not shown, and ROM, RAM and I/O port are connected to the CPU via bus lines. Control programs and various map data are stored in the ROM, and data which has been processed in the CPU is temporarily stored in the RAM. In addition, a switch 24 adapted to be controlled by the occupant is provided in the main unit 13, and an operation signal is inputted from the switch 24 into the CPU via the I/O port. In addition, in response to the operation of the switch by the occupant, an on/off signal and an aroma selection signal are outputted, whereby the supply apparatus 10 is switched between an operating state and a halt state by the on/off signal, while types of efficacious constituents to be loaded in the air gun 16 are switched by the aroma selection signal.

Figure 4:
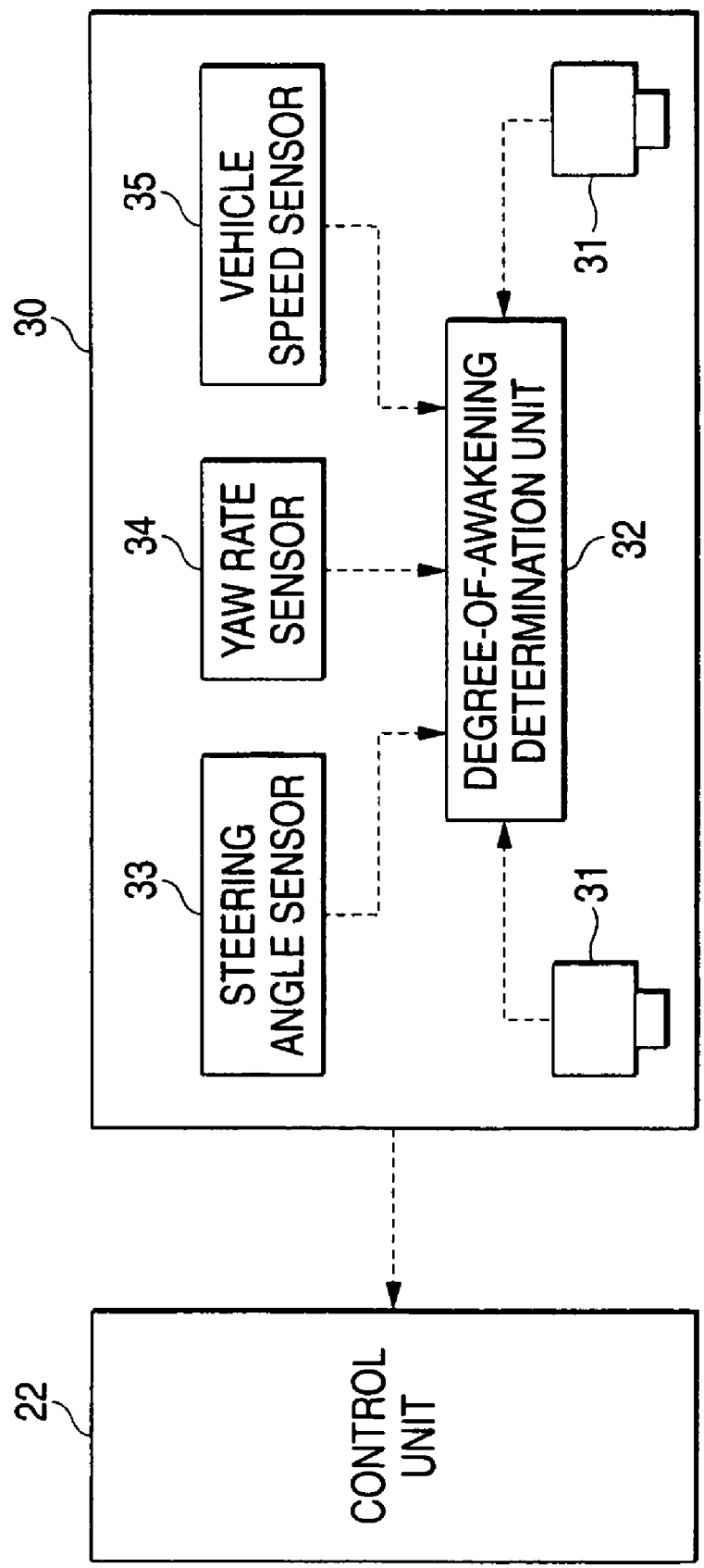
FIG. 4 is a block diagram showing the configuration of a driving condition detection unit.

In addition, a driving condition detection unit 30 as an awakening detection section for detecting a degree of awakening of the driver (occupant) is built in the main unit. Here, FIG. 4 is a block diagram showing the configuration of the driving condition detection unit 30. As is shown in FIG. 4, the driving condition detection unit 30 includes a stereoscopic camera 31 which captures an image in front of the vehicle and a degree-of-awakening determination unit 32 for processing an image signal from the stereoscopic camera 31. In addition, a steering angle sensor 33 for detecting a steering angle of a steering wheel, a yaw rate sensor 34 for detecting a yaw rate of the vehicle and a vehicle speed sensor 35 for detecting a vehicle speed are provided in the driving condition detection unit 30, and detection signals from these sensors 33 to 35 are inputted into the degree-of-awakening determination unit 32.

The degree-of-awakening determination unit 32 estimates a behavior of the vehicle based on an image signal from the stereoscopic camera 31, a steering angle signal from the steering angle sensor 33, a yaw rate signal from the yaw rate sensor 34 and a vehicle speed signal from the vehicle speed sensor 35, and makes a general determination on the degree of awakening of the driver based on the behavior of the vehicle so estimated. In addition, the degree of awakening determined by the degree-of-awakening determination unit 32 is inputted into the control unit 22, and this information on the degree of awakening is designed to be used for a projection mode switching control for curing rings V1, V2, which will be described later. Note that while in the description made above, the degree of awakening of the driver is determined from the and hence, the degree of awakening of the driver may be determined based on the behavior of the line of sight by detecting the behavior of the line of sight (the motion of the eyeballs) of the driver using a view camera or an infrared lamp.

Next, a projection mode switching control for curling rings V1, V2, which is executed by the control unit 22, will be described. The supply apparatus 10 shown includes as projection modes for curling rings V1, V2 an efficacious mode which is applied in a condition where the degree of awakening (attentiveness) of the driver is not reduced and an alarming mode which is applied in a condition where the degree of awakening of the driver is reduced. Here, FIG. 5 is an explanatory drawing showing an example of projecting conditions of curling rings V1, V2 in the efficacious mode, and FIG. 6 is an explanatory drawing showing an example of projecting conditions of curing rings V1, V2 in the alarming mode.

Figure 5:
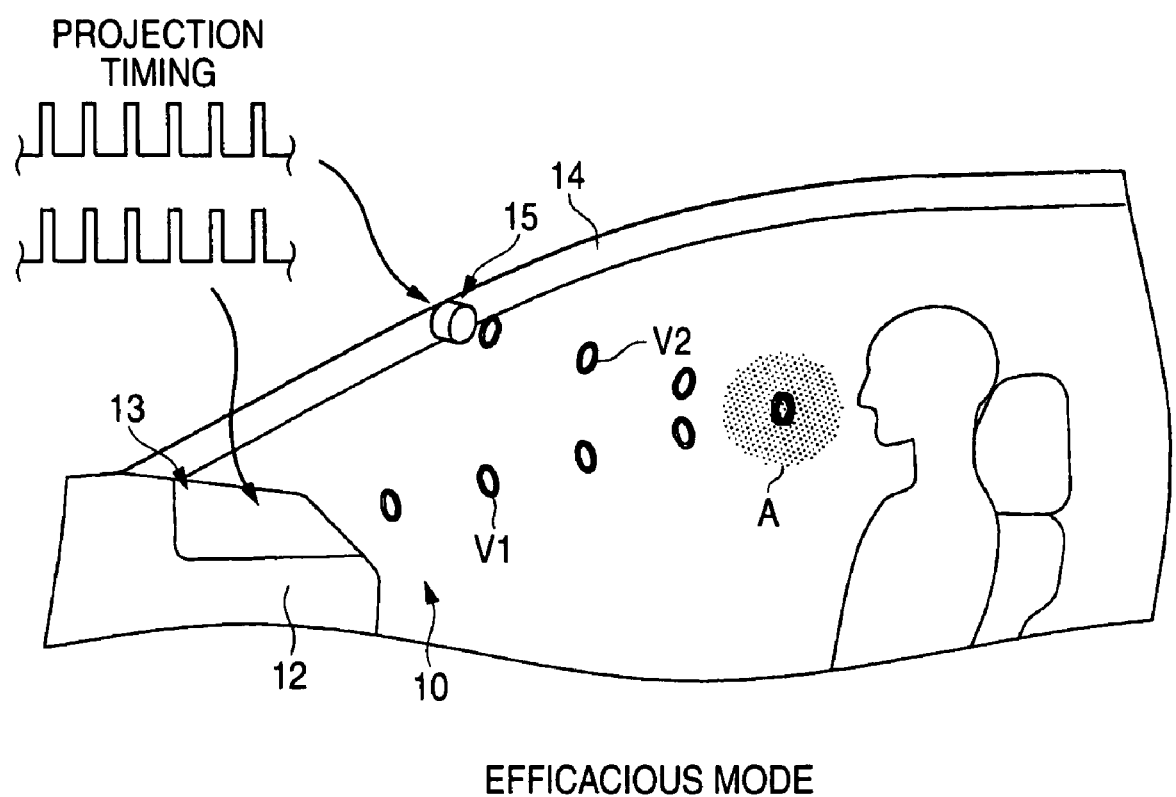
FIG. 5 is an explanatory drawing showing an example of projecting conditions of curling rings in an efficacious mode.

In a condition where the degree of awakening of the driver is not reduced, that is, in a condition where driving operations are carried out by the driver with safety, as is shown in FIG. 5, the efficacious mode is executed in which curling rings V1, V2 are caused to collide against each other so as to diffuse aromatic constituents. Namely, in this efficacious mode, since both curling rings V1, V2 are projected at substantially the same projection intervals so as to be controlled to collide against each other in the efficacious area A, only the efficacious constituents can be supplied to the occupant without causing him or her to feel a sensation of physical disorder due to air pressure. In addition, the timings at which curling rings V1, V2 are projected and types of aromatic constituents to be contained in curing rings V1 are set according to the switch control by the occupant.

Figure 6A:
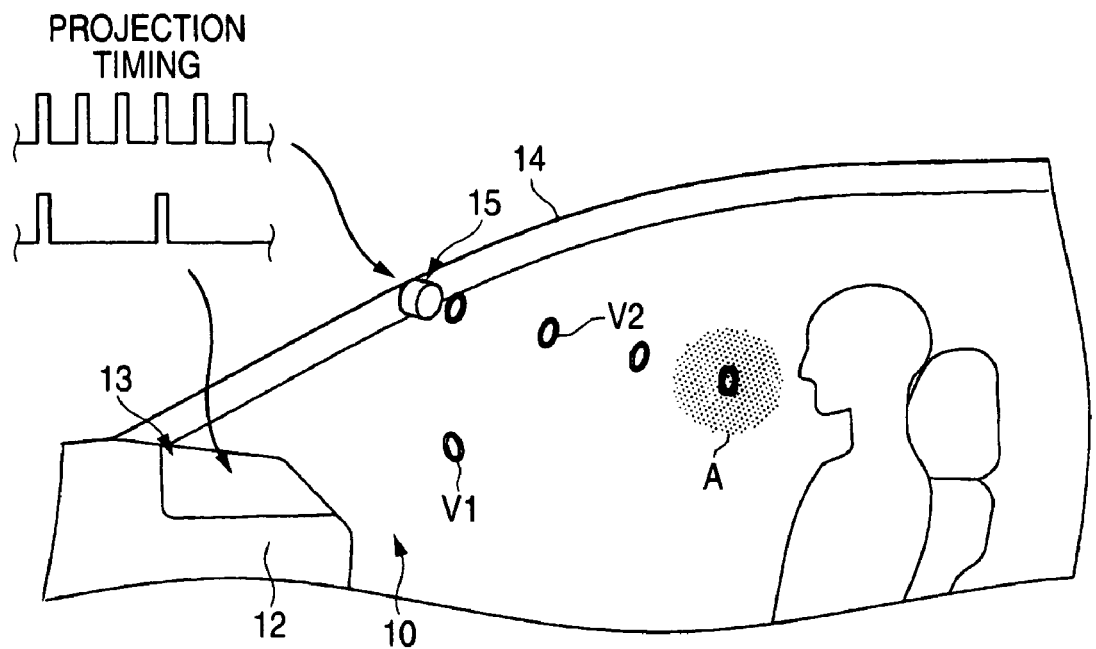
FIGS. 6A and 6B are explanatory drawings showing an example of projection conditions of curling rings in an alarming mode.
Figure 6B:
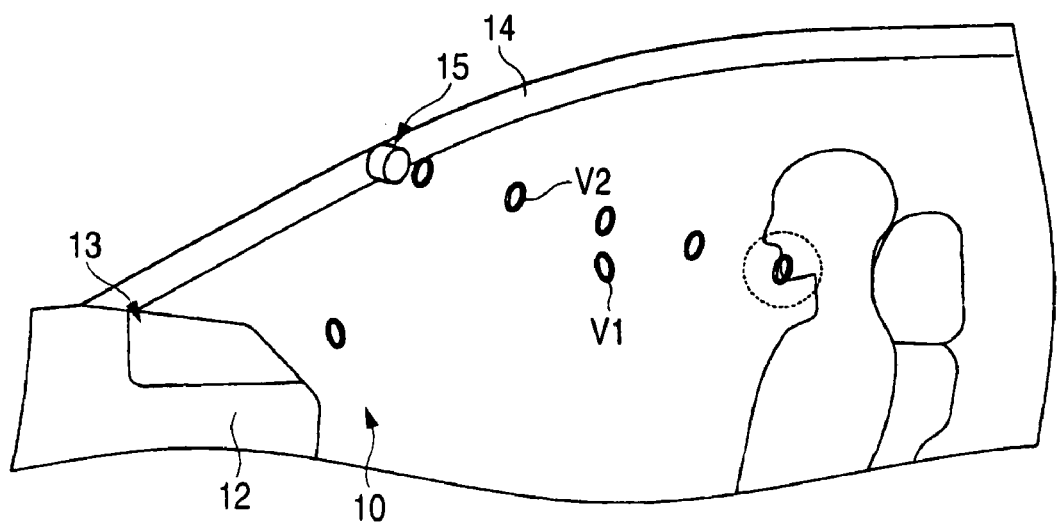

On the other hand, in a condition where the degree of awakening of the driver is reduced, that is, in a condition where the safety driving operations are not performed by the driver, the alarming mode is executed in which some of curling rings V2 are made not to collide against curing rings V1 so as to be applied to the driver as is shown in FIG. 6. Namely, in this alarming mode, since a projection interval at which curling rings V1 are projected is set shorter than a projection interval at which curling rings V2 are projected as is shown in FIG. 6A, some of curling rings V2 are allowed to exist in the efficacious area A so as to continue moving towards the driver for collision against him or her as shown in FIG. 6B. The driver can be given stimuli with curling rings V2 by executing the alarming mode, thereby making it possible to enhance the degree of awakening of the driver, whereby an accident can be prevented that would otherwise be caused due to the driver falling in a doze. In addition, in the alarming mode, mint-based or citrus fruit-based aromatic constituents having an awakening effect are adopted as aromatic constituents to be diffused, whereby the driver can be given not only touching stimuli but also smelling stimuli so as to realize a further enhancement of the safety in driving.

Figure 7A:
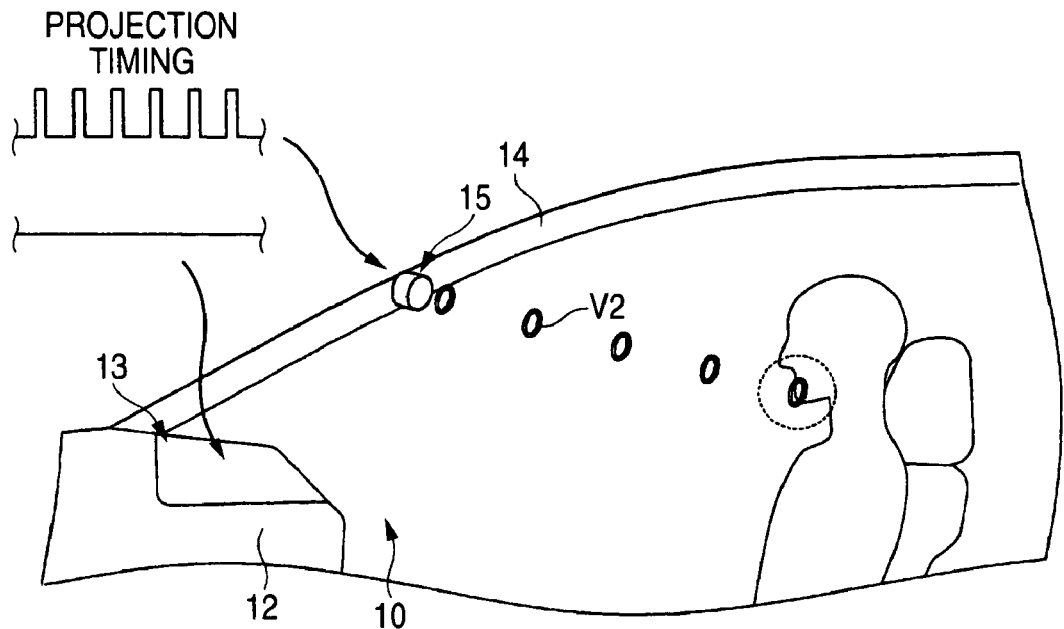
FIGS. 7A and 7B are explanatory drawings showing another example of projection conditions of curling rings in the alarming mode.
Figure 7B:
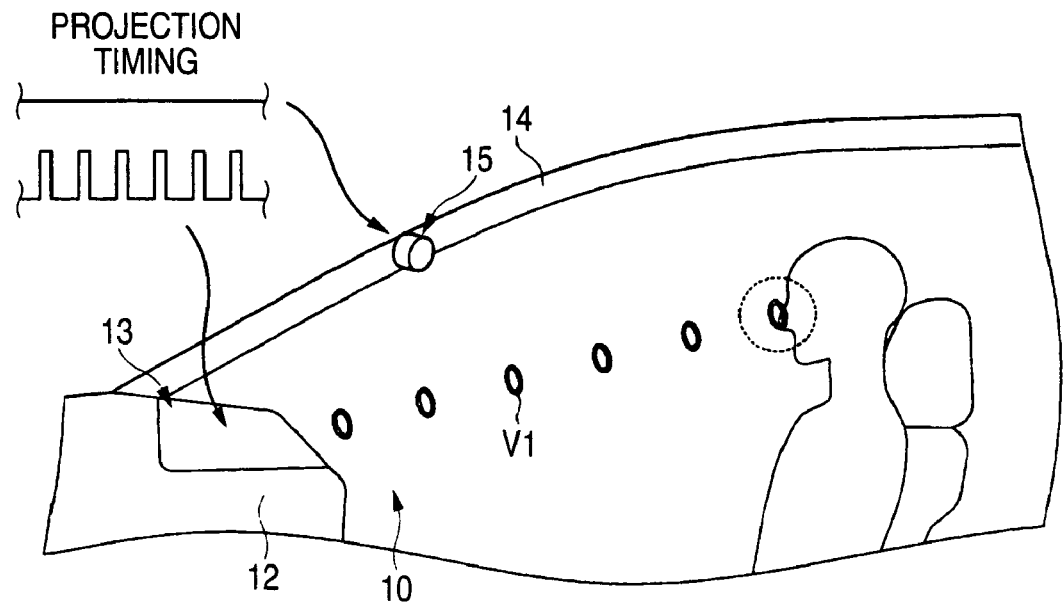

As to projection timings of curling rings V1, V2 in the alarming mode, the invention is not limited to the projection timings shown in FIG. 6, and hence, projection intervals and projection frequencies of curling rings V1, V2 can be altered as required according to the degree of awakening of the driver. Here, FIGS. 7A, 7B are explanatory drawings showing another example of projecting conditions of curing rings V1, V2 in the alarming mode. As is shown in FIG. 7A, only curling rings V2 may be projected without projecting any curling rings V1, whereas as is shown in FIG. 7B, only curling rings V1 may be projected without projecting any curling rings V2. For example, in a case where the degree of awakening of the driver is reduced remarkably, by adopting the projection timings shown in FIGS. 7A, 7B, many stimuli can be given to the driver so as to keep the driver awakened sufficiently for safety driving.

Figure 8:
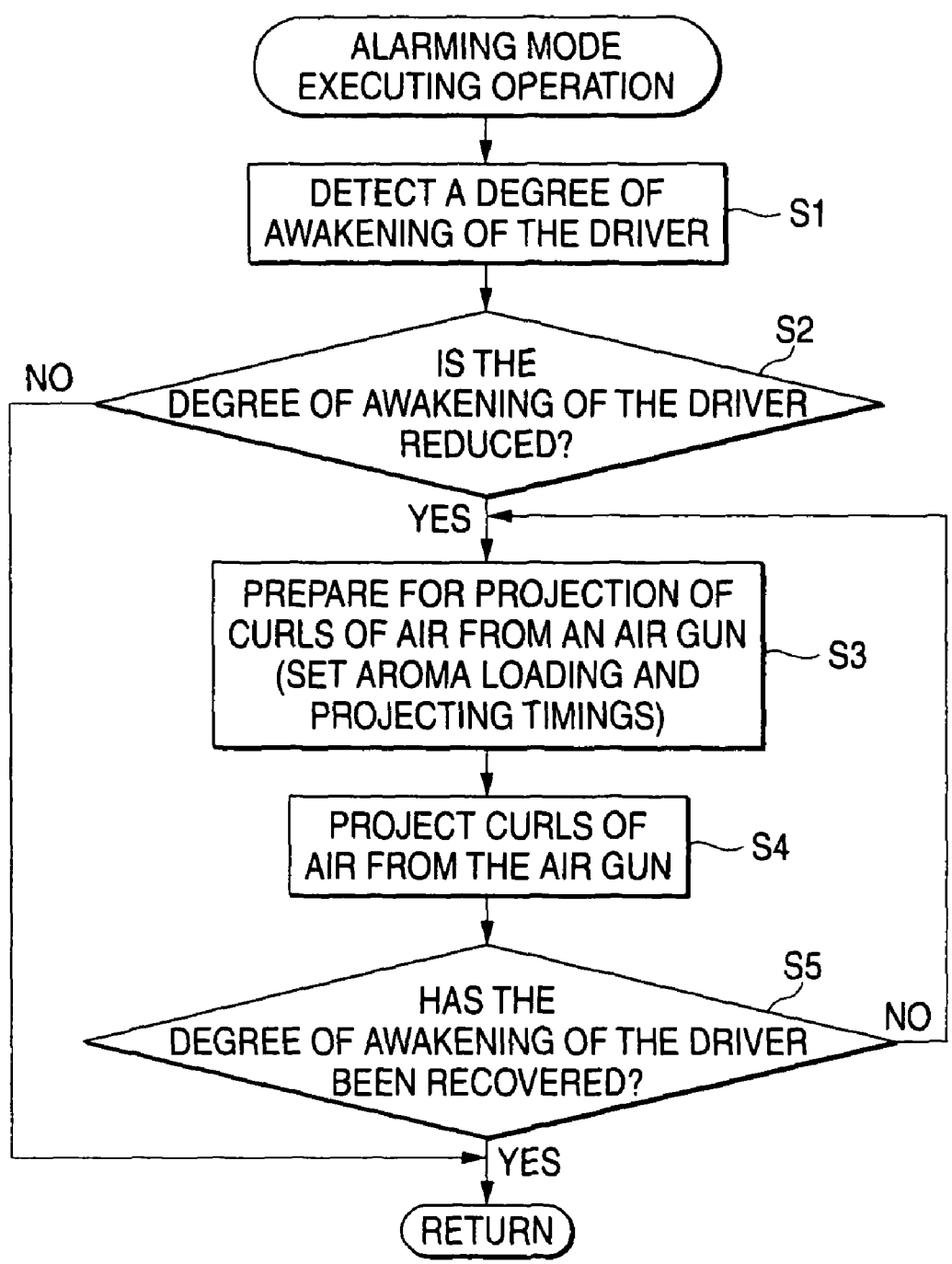
FIG. 8 is a flowchart illustrating an execution procedure of the alarming mode.

Next, an executing procedure of the alarming mode that has been described above will be described while following a flowchart. Here, FIG. 8 is a flowchart illustrating an execution procedure of the alarming mode. As is shown in FIG. 8, at step S1, the degree of awakening of the driver is detected by the driving condition detection unit 30, and at the following step S2, whether or not the degree of awakening of the driver is below a predetermined level. Then, if it is determined at step S2 that the degree of awakening of the driver is below the predetermined level and hence, the driving operations are not performed by the driver with safety, the flow proceeds to step S3, where preparations for projecting curling rings V1, V2 to the alarming mode are started. On the other hand, if it is determined at step S2 that the degree of awakening of the driver is above the predetermined level and that the driving operations are performed by the driver with safety, the flow leaves the routine without executing the alarming mode.

At step S3, projection timings for curling rings V1, V2 are set according to the degree of awakening of the driver that is detected by the driving condition detection unit 30, and a type of aromatic constituent that is to be loaded in the air gun 16 is set. Then, control signals are outputted from the control unit 22 to the efficacious gas generating unit 20 and the efficacious gas loading unit 21, and the loading of aromatic constituents in the air gun 16 is started. Following this, the flow proceeds to step S4, where projection timings are inputted into the driving circuit portion 18, whereby curling rings V1, V2 for the alarming mode are projected from the air guns 16, 17, respectively.

At the following step S5, whether or not the degree of awakening of the driver has been recovered by executing the alarming mode is determined. In step S5, if it is determined at step S5 that the degree of awakening of the driver has been recovered, since there exists currently a state in which the safe driving operations have just been resumed, the alarming mode is ended, the flow leaving the routine. On the other hand, it is determined at step S5 that the degree of awakening of the driver has not yet been recovered, the alarming mode in which curling rings V2 are applied to the driver is executed again from step S3 until the safe driving operations are resumed.

Note that while in the description above, aromatic constituents are described as being generated as efficacious constituents, the invention is not limited thereto, and hence, microscopic mists (moisture constituents, minute water particles floating in the air) which can give the occupant a wetting and refreshing sensation may be generated as efficacious constituents. In addition, ozone having a deodorizing effect may be generated as efficacious constituents, and oxygen which has an awakening effect on the occupant may be generated as efficacious constituents. Namely, for the efficacious gas generating unit 20, a mist generating mechanism may be provided for generating microscopic mists by virtue of ultrasonic vibrations, an ozone generating mechanism may be provided for generating ozone ($O_3$) by virtue of silent discharge, or an oxygen adding mechanism may be provided for enhancing the oxygen contents by means of an oxygen enrichment membrane.

The invention is not limited to the embodiment that has been described heretofore but may, needless to say, be modified variously without departing the spirit and scope thereof. For example, while in the above description, the subunit 15 is installed in the front pillar portion 14, the invention is not limited thereto, and hence, the subunit 15 may be installed on a front roof rail portion which lies above the windshield or the subunit 15 may be installed in a corner of the instrument panel portion 12. Similarly, while the main unit 13 is installed substantially in the center of the instrument panel portion 12, the invention is not limited thereto, and hence, the main unit 13 may be installed in other locations. Furthermore, needless to say, the main unit 13 and the subunit 15 may be incorporated into a single unit.

In addition, while in the description made before, curling rings V1, V2 are made to be projected from the air guns 16, 17 by causing the rod member 16d to protrude by driving the electric motor, the invention is not limited to this construction, and hence, curing rings V1, V2 may be made to be projected from the air guns 16, 17 by virtue of electromagnetic force by building an electromagnetic coil and a movable iron core in the air guns 16, 17. In addition, while the air guns 16, 17 include the corrugated pump main bodies 16a, 17a, respectively, a diaphragm may be used to push out air. Furthermore, while annular curling rings V1, V2 are illustrated as being projected from the air guns 16, 17, respectively, the shape of the first curl of air and the second curl of air is not limited to the annular shape, and hence, a curl of air can be formed into any shape, provided that a certain amount of air can be delivered in a well-arranged fashion.

Note that while the air guns 16, 17 are illustrated as being fixed, the air guns 16, 17 may be made to be rotated using an electric motor or the like. In this way, by adopting the construction in which the air guns 16, 17 can be rotated, curling rings V1, V2 can be applied to the driver in a more exact fashion when executing the alarming mode. Furthermore, even in the event that the efficacious mode is performed, an appropriate efficacious area A can be set for each of the occupants.

[FIG. 2]
23: air inlet port
20: efficacious gas generating unit
21: efficacious gas loading unit
18: driving circuit portion
22: control unit
24: switch
30: driving condition detection unit
[FIG. 4]
22: control unit
33: steering angle sensor
34: yaw rate sensor
35: vehicle speed sensor
32: degree-of-awakening determination unit
[FIG. 5]
A1: Projection timing
A2: efficacious mode
[FIG. 6]
A1: Projection timing
A2: alarming mode
[FIG. 7]
A1: Projection timing
A2: alarming mode
[FIG. 8]
A1: Alarming mode executing operation
S1: detect a degree of awakening of the driver
S2: Is the degree of awakening of the driver reduced?
S3: prepare for projection of curls of air from an air gun (set aroma loading and projecting timings)
S4: project curls of air from the air gun
S5: Has the degree of awakening of the driver been recovered?
A2: return

What is claimed is:

1. A vehicle efficacious constituents supply apparatus, comprising:
   a first projecting section for projecting a first curl of air towards a first predetermined position;
   a second projecting section for projecting a second curl of air towards a second predetermined position;
   a constituents supply section for supplying efficacious constituents to at least either of the first curl of air and the second curl of air; and
   a projection control section for controlling projection timings of the first curl of air and the second curl of air,
   wherein the projection control section is configured to control the first projecting section second protecting section in projection modes including an efficacious mode in which efficacious constituents are diffused by causing the first curl of air and the second curl of air to collide with each other and an alarm mode for causing at least either of the first curl of air and the second curl of air to collide against an occupant without causing the curls of air to collide with each other.

2. The vehicle efficacious constituents supply apparatus as set forth in claim 1, further comprising an awakening detection section for detecting a degree of awakening of the occupant,
   wherein the projection control section executes the alarm mode based on the degree of awakening of the occupant.

3. The vehicle efficacious constituents supply apparatus as set forth in claim 1, wherein the first predetermined position and the second predetermined position are identical.

4. The vehicle efficacious constituents supply apparatus as set forth in claim 1, wherein the efficacious constituents comprise at least one of aromatic constituents, microscopic mists, ozone and oxygen.

5. The vehicle efficacious constituents supply apparatus as set forth in claim 1, wherein the projection control section sets a projection timing of the first curl of air equal to a projection timing of the second curl of air in the efficacious mode and sets the projection timing of the first curl of air to be shorter than the projection timing of the second curl of air in the alarm mode.

6. The vehicle efficacious constituents supply apparatus as set forth in claim 1, wherein the first curl of air and the second curl of air collide with each other in an efficacious area which is set in front of a nose of the occupant.

7. A method of providing efficacious constituents to an occupant in a vehicle, the method comprising:
   determining a degree of awakening of the occupant;
   projecting a first curl of air and a second curl of air to collide with each other when said determining determines that the degree of awakening of the occupant is not reduced; and
   projecting the first curl of air and the second curl of air not to collide with each other and to collide against the occupant when said determining determines that the degree of awakening of the occupant is reduced.

8. The method according to claim 7, further comprising providing aromatic constituents in said first curl of air and said second curt of air.

9. The method according to claim 8, wherein the projecting of the first curl of air and the second curl of air are supplied with one of a mint or citrus fruit-based aromatic constituents when said determining determines that the degree of awakening of the occupant is reduced.

10. The method according to claim 7, wherein when said determining determines that the degree of awakening of the occupant is reduced, a projection timing of the first curl of air is set shorter than a projection timing of the second curl of air.

11. The method according to claim 7, wherein when said determining determines that the degree of awakening of the occupant is not reduced, a projection timing of the first curl of air is set equal to a projection timing of the second curl of air.

12. The method according to claim 7, wherein the projecting of the first curl of air and the second curl of air to collide with each other in an efficacious area is set in front of a nose of the occupant.

13. The method according to claim 7, wherein the determining of the degree of awakening of the occupant comprises measuring at least one of a steering wheel angle, a yaw rate sensor output, a vehicle speed sensor, and a stereoscopic camera image from a front of a vehicle.

* * * * *